(12) United States Patent
Baynham et al.

(10) Patent No.: US 7,186,255 B2
(45) Date of Patent: Mar. 6, 2007

(54) POLYAXIAL SCREW

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 156 days.

(21) Appl. No.: 10/918,517

(22) Filed: Aug. 12, 2004

(65) Prior Publication Data

US 2006/0036252 A1    Feb. 16, 2006

(51) Int. Cl.
*A61B 17/58*    (2006.01)
*A61F 2/30*    (2006.01)

(52) U.S. Cl. .......................... 606/61; 606/73
(58) Field of Classification Search ................. 606/72, 606/73, 61
See application file for complete search history.

(56) References Cited

U.S. PATENT DOCUMENTS

| | | | |
|---|---|---|---|
| 1,410,480 A * | 3/1922 | Landgraf ..................... 411/381 |
| 2,414,882 A * | 1/1947 | Longfellow ................... 606/65 |
| 4,463,753 A * | 8/1984 | Gustilo ......................... 606/73 |
| 4,653,481 A | 3/1987 | Howland et al. |
| 4,805,602 A | 2/1989 | Puno et al. |
| 4,887,596 A | 12/1989 | Sherman |
| 4,946,458 A | 8/1990 | Harms et al. |
| 4,987,892 A | 1/1991 | Krag et al. |
| 5,000,165 A | 3/1991 | Watanabe |
| 5,002,542 A | 3/1991 | Frigg |
| 5,030,220 A | 7/1991 | Howland |
| 5,102,412 A | 4/1992 | Rogozinski |
| 5,190,543 A | 3/1993 | Schlapfer |
| 5,207,678 A | 5/1993 | Harms et al. |
| 5,209,753 A | 5/1993 | Biedermann et al. |
| 5,217,497 A | 6/1993 | Mehdian |
| 5,242,443 A | 9/1993 | Kambin |
| 5,306,275 A | 4/1994 | Bryan |
| 5,344,422 A | 9/1994 | Frigg |
| 5,360,431 A | 11/1994 | Puno et al. |
| 5,395,371 A | 3/1995 | Miller et al. |
| 5,466,237 A | 11/1995 | Byrd, III et al. |
| 5,496,321 A | 3/1996 | Puno et al. |
| 5,501,684 A * | 3/1996 | Schlapfer et al. ............. 606/73 |
| 5,520,689 A | 5/1996 | Schlapfer et al. |
| 5,540,690 A | 7/1996 | Miller et al. |
| 5,545,163 A | 8/1996 | Miller et al. |
| 5,571,102 A | 11/1996 | Cavagna et al. |
| 5,584,831 A | 12/1996 | McKay |

(Continued)

*Primary Examiner*—Corrine McDermott
*Assistant Examiner*—Thomas J Sweet
(74) *Attorney, Agent, or Firm*—McHale & Slavin PA

(57) ABSTRACT

A polyaxial screw is used to secure orthopedic appliances to bone, particularly the spine. The polyaxial screw has a shaft including a helical screw thread for securing the screw to bone. One end of the shaft has a reverse tapered head tapering toward and away from the shaft from an enlarged median. A spherical shaped swivel, having an opening smaller than the median, is snapped over the head to rotatably engage the shaft. A connector with a dome shaped cavity on one end and bifurcated tabs on the other is connected with the swivel and tightened in place with a set screw and guide ring. An appliance is held between the bifurcated tabs. The tabs are frangible to reduce the profile above the appliance.

14 Claims, 6 Drawing Sheets

U.S. PATENT DOCUMENTS

| | | |
|---|---|---|
| 5,584,887 A | 12/1996 | Kambin |
| 5,593,407 A | 1/1997 | Reis |
| 5,624,442 A | 4/1997 | Mellinger et al. |
| 5,628,740 A | 5/1997 | Mullane |
| 5,643,262 A | 7/1997 | Metz-Stavenhagen et al. |
| 5,683,390 A | 11/1997 | Metz-Stavenhagen et al. |
| 5,725,528 A | 3/1998 | Errico et al. |
| 5,735,851 A | 4/1998 | Errico et al. |
| 5,746,741 A * | 5/1998 | Kraus et al. .................. 606/54 |
| 5,782,833 A | 7/1998 | Haider |
| 5,800,435 A | 9/1998 | Errico et al. |
| 5,814,046 A | 9/1998 | Hopf |
| 5,879,351 A | 3/1999 | Viart |
| 5,910,142 A | 6/1999 | Tatar |
| 5,989,254 A | 11/1999 | Katz |
| 6,001,098 A | 12/1999 | Metz-Stavenhagen et al. |
| 6,004,322 A | 12/1999 | Bernstein |
| 6,063,090 A | 5/2000 | Schlapfer |
| 6,090,110 A | 7/2000 | Metz-Stavenhagen |
| 6,113,601 A | 9/2000 | Tatar |
| 6,139,549 A | 10/2000 | Keller |
| 6,146,383 A * | 11/2000 | Studer et al. ................ 606/61 |
| 6,179,838 B1 | 1/2001 | Fiz |
| 6,183,472 B1 | 2/2001 | Lutz |
| 6,187,005 B1 * | 2/2001 | Brace et al. .................. 606/61 |
| 6,214,006 B1 | 4/2001 | Metz-Stavenhagen |
| 6,241,731 B1 * | 6/2001 | Fiz .............................. 606/65 |
| 6,248,105 B1 | 6/2001 | Schlapfer et al. |
| 6,261,287 B1 | 7/2001 | Metz-Stavenhagen |
| 6,280,443 B1 | 8/2001 | Gu et al. |
| 6,302,888 B1 | 10/2001 | Mellinger et al. |
| 6,325,802 B1 | 12/2001 | Frigg |
| 6,331,179 B1 * | 12/2001 | Freid et al. ................... 606/61 |
| RE37,665 E | 4/2002 | Ralph et al. |
| 6,371,957 B1 | 4/2002 | Amrein et al. |
| 6,402,752 B2 | 6/2002 | Schaffler-Wachter et al. |
| 6,413,257 B1 | 7/2002 | Lin et al. |
| 6,423,064 B1 | 7/2002 | Kluger |
| 6,482,207 B1 | 11/2002 | Errico |
| 6,485,494 B1 | 11/2002 | Haider |
| 6,520,963 B1 | 2/2003 | McKinley |
| 6,533,790 B1 | 3/2003 | Liu |
| 6,537,276 B2 | 3/2003 | Metz-Stavenhagen |
| 6,554,831 B1 | 4/2003 | Rivard et al. |
| 6,554,834 B1 | 4/2003 | Crozet et al. |
| 6,616,668 B2 | 9/2003 | Altarac et al. |
| 6,623,485 B2 | 9/2003 | Doubler et al. |
| 6,641,586 B2 | 11/2003 | Varieur |
| 6,648,888 B1 | 11/2003 | Shluzas |
| 6,669,697 B1 | 12/2003 | Pisharodi |
| 6,835,196 B2 * | 12/2004 | Biedermann et al. ......... 606/61 |
| 2002/0143341 A1 * | 10/2002 | Biedermann et al. ......... 606/73 |
| 2003/0130659 A1 * | 7/2003 | Haider ........................ 606/61 |
| 2005/0004574 A1 * | 1/2005 | Muckter ...................... 606/69 |
| 2005/0049588 A1 * | 3/2005 | Jackson ....................... 606/61 |
| 2005/0049589 A1 * | 3/2005 | Jackson ....................... 606/61 |
| 2005/0055026 A1 * | 3/2005 | Biedermann et al. ......... 606/73 |
| 2005/0182409 A1 * | 8/2005 | Callahan et al. .............. 606/72 |
| 2005/0216003 A1 * | 9/2005 | Biedermann et al. ......... 606/61 |
| 2006/0149240 A1 * | 7/2006 | Jackson ....................... 606/61 |

* cited by examiner

POLYAXIAL SCREW

BACKGROUND OF THE INVENTION

1. Field of the Invention

This invention relates to the field of orthopedic surgery and, particularly to modular screws having a polyaxial head.

2. Description of the Prior Art

It is conventional to install surgical appliances, such as rods or plates, to correct skeletal deformities and injuries in which the appliance spans several vertebrae. The surgical appliance is secured to the vertebrae and maintains a stable spatial relationship between them. Pedicle screws are inserted into the vertebrae to anchor the appliance in place. Because of the non-uniform anatomy of the vertebrae, the screws are usually misaligned relative to each other. To compensate for these variances, the rods may be bent to match the location of the screws or the screws may have connectors capable of angular displacement to engage the rods or both.

For example, U.S. Pat. No. 6,669,697 to Pisharodi teaches the use of eccentric shims between the bone screws and the surgical appliance to correct the angle between the rod and the screw. Shluzas, U.S. Pat. No. 6,648,888, teaches a bone screw with a spherical head rotating in a tapered connector. The connector has opposing tabs to capture the spinal rod and a set screw to hold the rod in the yoke. Reissued patent, RE37,665, teaches another spherical headed screw with a swiveling connector having an upstanding yoke capturing a spinal rod. Varieur, U.S. Pat. No. 6,641,586, teaches another spherical headed bone screw and an upstanding yoke retainer for the surgical appliance. The retainer has an internal nut and an external ring threaded onto the yoke to secure the appliance. These devices all have a multitude of small parts that must be assembled at the surgical site.

SUMMARY OF THE PRESENT INVENTION

The polyaxial screw of the instant invention has a helical screw shaft for securing the screw to bone. One end of the shaft has a reverse tapered head tapering toward and away from the shaft from an enlarged median. A spherical shaped swivel, having an opening smaller than the median, is placed over the head to rotatably engage the shaft. The swivel frictionally engages the head. A connector with a dome shaped cavity on one end and bifurcated tabs on the other is connected with the swivel and tightened in place with a set screw and guide ring. An appliance is held between the bifurcated tabs. The tabs are frangible to reduce the profile above the appliance.

It is therefore an objective of this invention to provide a modular polyaxial screw assembly having a few large parts which can be easily handled and quickly connected during surgery.

It is another objective of this invention to provide a polyaxial screw assembly having the ability of being angularly fixed in place and connected to a surgical appliance with one tool.

It is another objective of this invention to provide a low profile surgical appliance.

It is yet another objective of this invention to provide a device to prevent cross threading of components.

It is a further objective of this invention to provide an assembly permitting a small screw head.

It is still another objective of this invention to provide a bone screw that creates a buttress seat in the vertebrae through rotation of an integral flange.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
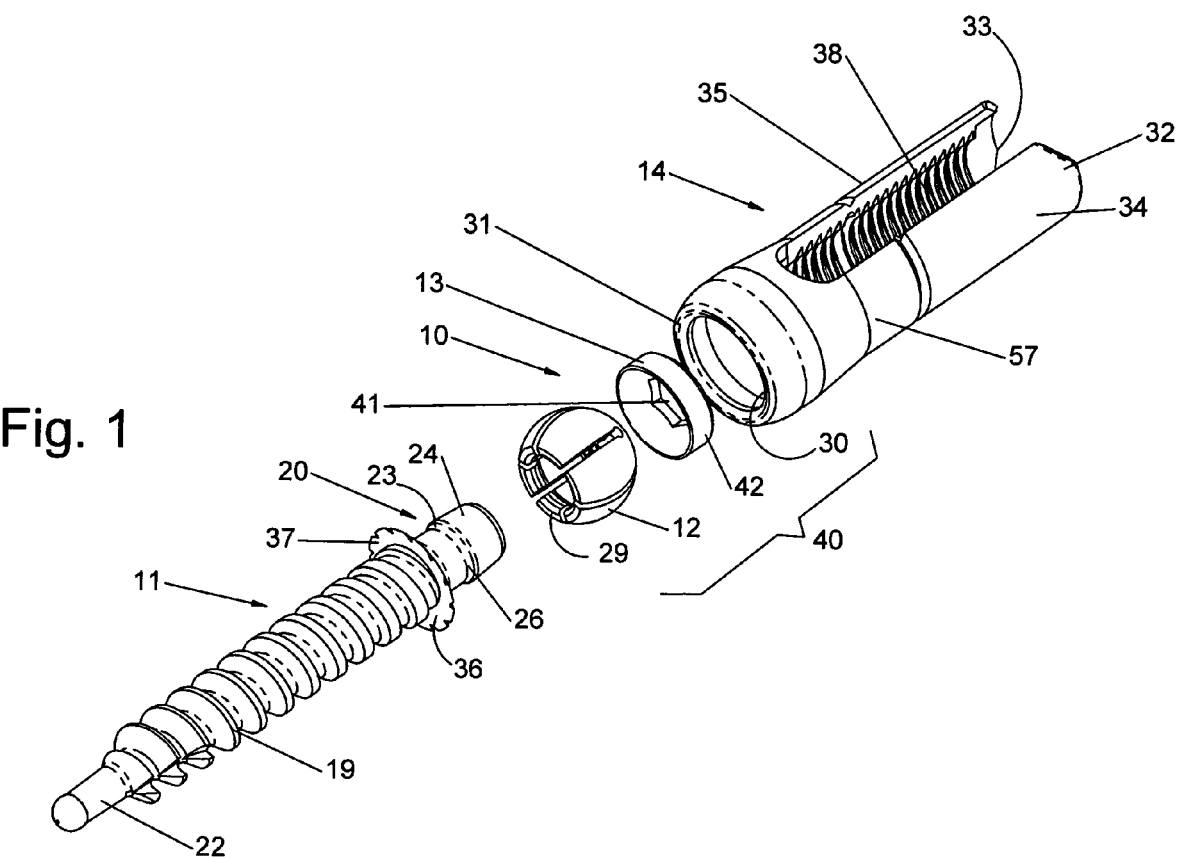
FIG. 1 is an exploded perspective of the polyaxial screw of this invention.
Figure 2:
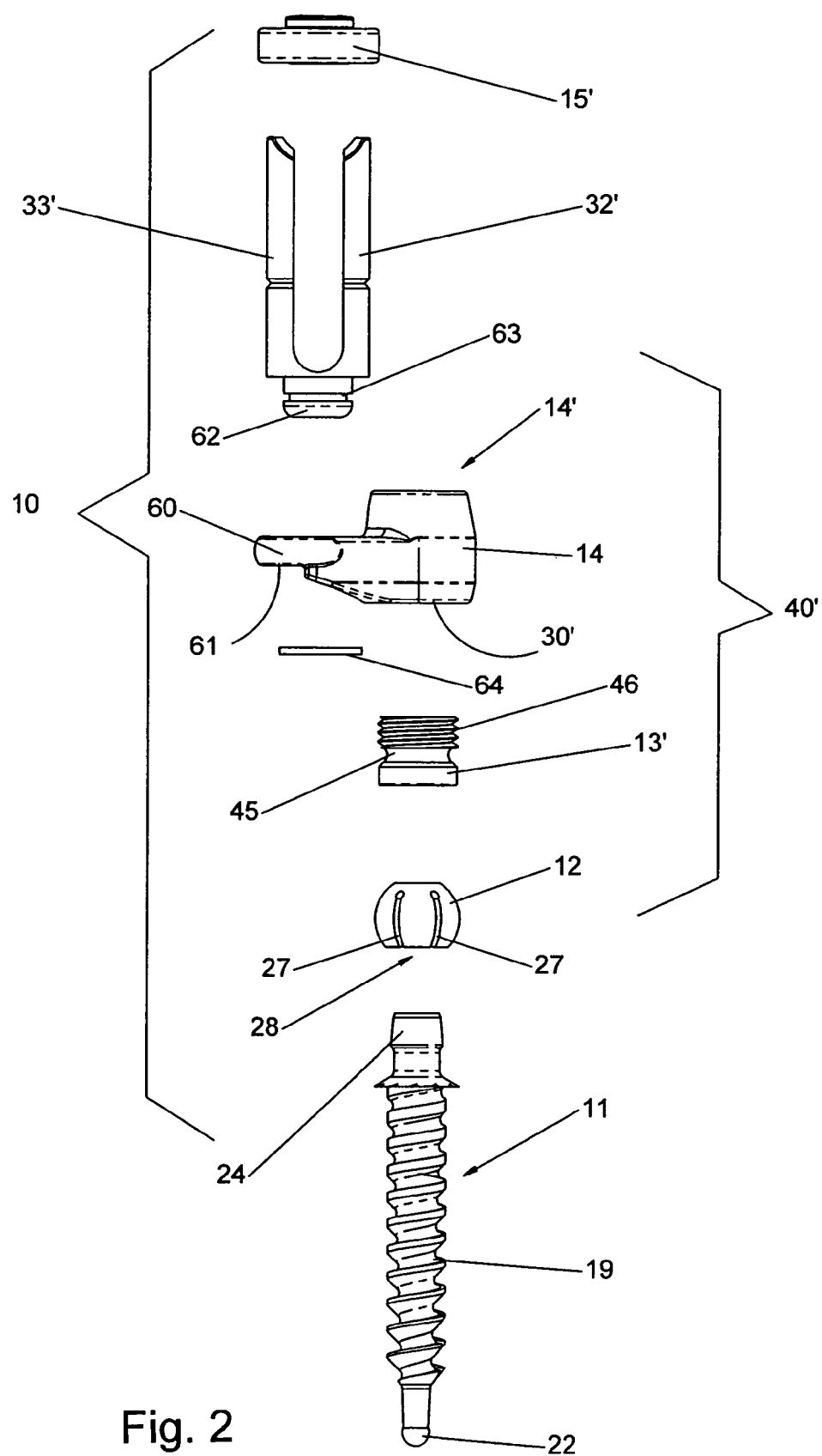
FIG. 2 is an exploded side view of the polyaxial screw with an off-set head.
Figure 3:
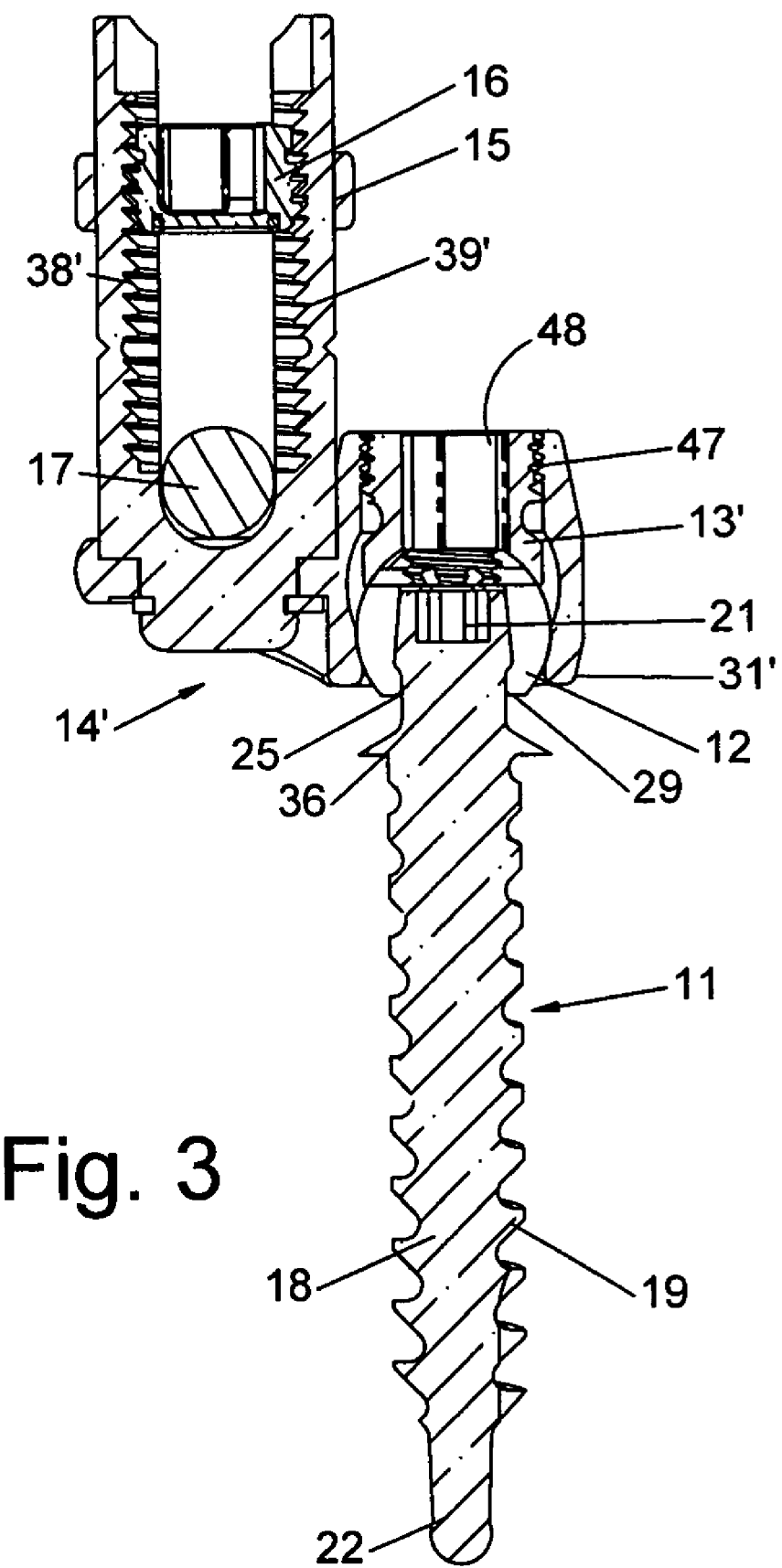
FIG. 3 is a longitudinal cross section of the assembled polyaxial screw of FIG. 2.

The polyaxial screw assembly 10, shown in FIGS. 1–2, is composed of a bone or pedicle screw 11, a collet or swivel 12, a ring or collar 13, 13', a connector 14, a guide or locking ring 15, and a set screw or nut 16. In FIG. 3, a surgical appliance, such as a spinal rod 17 is illustrated positioned between the connector 14 and the nut 16. The polyaxial screw assembly may be used in conjunction with spinal rods, hooks or other surgical appliances that require securement to the skeletal structure.

The bone screw 11, shown in FIGS. 1–3, has a shaft 18 having a helical thread 19 for drilling into the skeleton of a patient. A reverse tapered head 20 has a bore 21 for engagement with a tool (not shown) for turning the screw into the bone. The leading end 22 of the screw may be self tapping or used with pre-drilled holes. The head 20 has its greatest diameter at the shoulder 23. The head has a taper 24 from the shoulder toward the leading end and another taper 25 from the shoulder toward the head end. A cylindrical groove 26 circumscribes the screw 11 and forms a retention ring for the swivel 12. Between the groove 26 and the threads 19, a buttress flange 36 extends circumferentially around the head with radial serrations 37. As the pedicle screw is turned into the vertebrae, the buttress flange 36 of the screw will contact the cortical bone and rotationally groom the bone to accept the seating of the screw against the vertebra body and provide space between the bone and the head. This serves to stabilize the head of the screw against the hard outer shell of the vertebrae and prevents the bone from interfering with the completion of the assembly. The serrations 37 shear away any bony protuberances resulting in a flat bed for the screw. The flange 36 also provides a depth gauge and stop for the screw.

Figure 4:
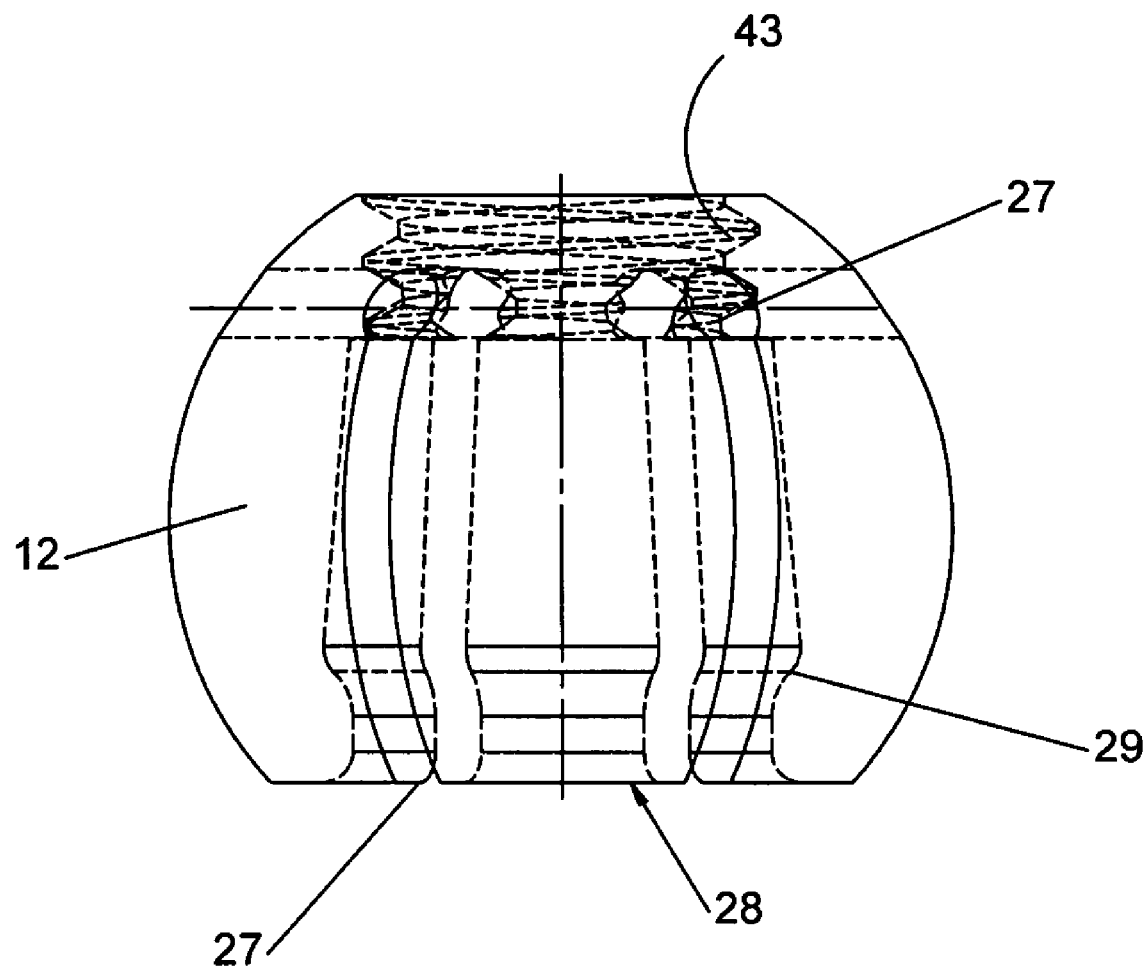
FIG. 4 is a perspective, partially in section, of the swivel of the polyaxial screw.

The swivel or collet 12, shown in FIGS. 1, 2 and 4, is generally spherical in shape, with an internal cavity, and has longitudinal slots 27 providing adjustability in size through compression. The swivel has a mouth 28 which is interrupted by the slots 27. The top of the collet, opposite the mouth, has an opening for insertion of a tool. The diameter of the mouth 28 is less than the diameter of the shoulder 23 on the head 20. The mouth has a lip 29 extending inwardly of the collet. The lip 29 is shaped to snap into the groove 26. The swivel and the screw will be held together by the elasticity of the collet.

The connector 14 and the swivel 12 can be pre-assembled as a subassembly to reduce the work load at the surgical site. Of course, this modular construction provides the flexibility of changing the size screw to fit the anatomical requirements of the patient. Once the screw and collet are assembled, the collet can rotate around the longitudinal axis of the screw. This construction permits a smaller screw head than the conventional solid spherical screw heads. The modularity allows different sized screws and different sized collets to be mixed and matched, given that the shoulder 23 of the screw and the mouth 28 of the collet are relatively sized to snap fit.

A universal connector 14, as shown in FIG. 1, has a dome shaped cavity 30 on one end. The ring 13 is inserted into the cavity 30. The cavity 30 has an opening 31 in one end to accept the collet. Before or after the assembled polyaxial screw is fixed in the bone, a collar 13, shown in FIG. 1, is inserted between the tabs 32, 33 into cavity 30 and in contact with the edge of the opening in the dome shaped cavity 30 of the connector 14. The collet 12 is inserted into cavity 30 and retains collar 13. The collet has a diameter greater than the diameter of the opening. The collar 13 has a central opening 41 with a circular extension 42 depending therefrom. The extension 42 is sized to contact the collet 12. The collar may also be pre-assembled with the connector assembly 40. The diameter of the circular extension 42 is somewhat less than the outer dimensions of the spherical collet 12. When the collet, the intermediate ring 13, and the connector are assembled, the collet is compressed to firmly secure the connector and the collet and the screw together. The top of the dome shaped cavity 30 is open and formed with directly opposed, parallel, semicircular tabs 32 and 33 extending normal to the opening 31. The outer surfaces 34 and 35 of the tabs are substantially smooth. Near the dome shaped cavity 30, both tabs 32 and 33 have sections 57 of a frangible ring. The ring may be a groove or separated dimples with the function of locating the level at which the tabs may be broken or otherwise separated to reduce the profile of the apparatus. The internal surfaces have threads 38 and 39 to translate a threaded locking screw along their length.

The swivel 12, ring 13, and the connector 14 may be pre-assembled with the screw 11 to provide a conveniently sized component for the surgeon's use. The continuous pathway through the tabs, the top of the dome, the ring, and the collet to the bore in the screw permits the assembly to be driven into the bone with one tool in one operation. The connector can then be rotated about the screw by means of the collet. The ball and socket fit between the connector and the collet allow universal movement in an arc of approximately 30 to 40 degrees.

Figure 5:
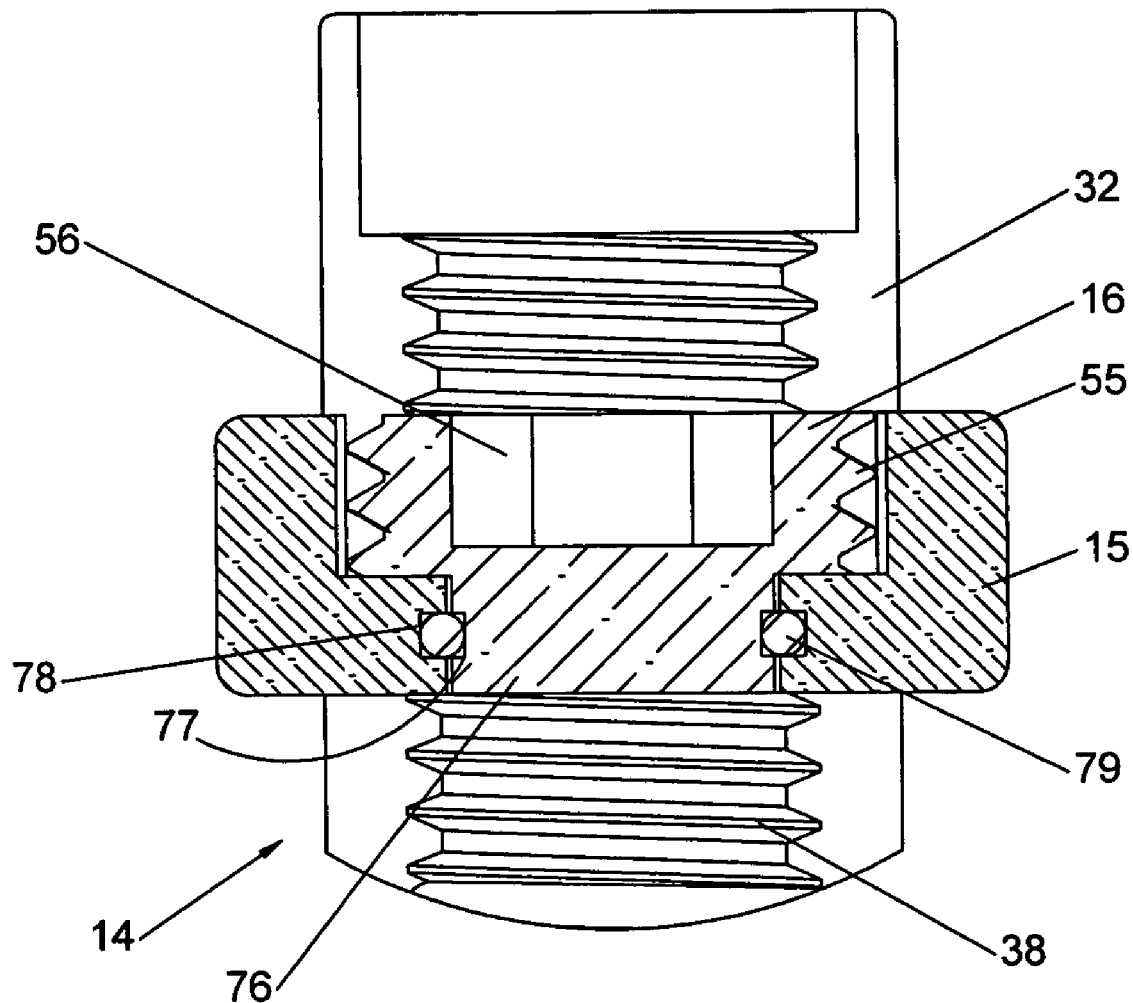
FIG. 5 is a cross section of the rod connector of the polyaxial screw.
Figure 6:
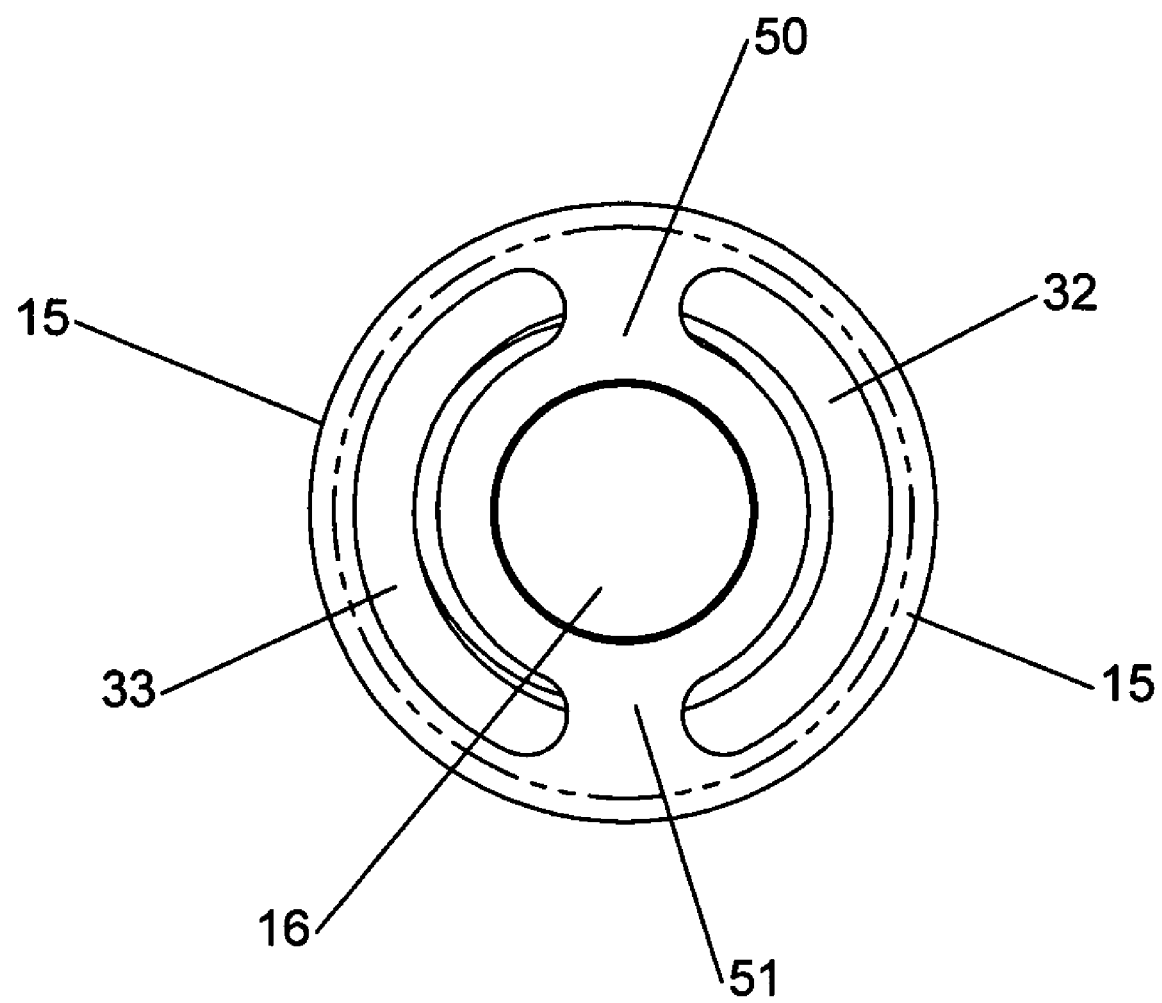
FIG. 6 is a top plan view of the lock nut and guide ring.

In this manner, a surgical appliance, such as a spinal rod 17, may be attached between the tabs of several misaligned screws. A guide ring 15, shown in FIG. 6, is telescoped over the tabs 32 and 33, after the spinal rod 17 is in place. The guide ring has an inner diameter approximately the same as the outer diameter of the tabs. The guide ring may orient the lock nut 16 in position relative to the tabs to prevent cross threading of the components. As an example, shown in FIG. 6, arms 50 and 51 are diametrically opposed and the arms are aligned with the gap between the tabs. In pre-assembly, the threads 55 of the lock nut 16, shown in FIG. 5, may be threaded into buttress screw threads 38 in these arms. The lock nut 16 is translated along the threads 38 to engage the rod 17 by a tool (not shown) engaged with the aperture 56. Arms 50 and 51 retain the set screw 16 by means of a groove 77 eliminating disassembly.

The guide ring 15 is placed about the tabs 32 and 33 and secured in place to reinforce the connector 14 diametrically. The lock nut 16 is tightened to positively fix the connector and the swivel 12 in a particular angular orientation with the surgical appliance held in place by the lock nut. However, it is within the purview of this apparatus to use more than one lock nut or collars or circular shims to vertically adjust the level of the surgical appliance within the tabs. The collar 13 serves as a compression ring with an area contact on the collet.

Once the proper sized screws and connectors are selected for a surgical procedure, the pre-assembly of modules permits the surgeon to manipulate and install a relatively large component having the bone screw, the collet, the connector and the collar as a unit. A tool similar to a screw driver may be inserted through the tabs of the connector the opening in the collar, and the opening in the collet to drive the screw into the bone. The connector may then be maneuvered to put the surgical appliance between the tabs. The guide ring 15 is then placed over the tabs and the locking nut is threaded onto the tabs and tightened in place against the surgical appliance forcing the surgical appliance the collar and the connector into a fixed position.

In the preferred embodiment, the pedicle screw is placed in the vertebrae and the assembly 40 composed of the collet 12, the collar 13 and the connector 14 is snapped on the tapered head into groove 26. Collet ridge 29 will expand beyond shoulder 23 and settle into groove 26. This action is uni-directional and will not reverse back off screw body. A tool (not shown)can accomplish the assembly and disassembly, if necessary. The collet 12 has screw threads 43 in the top to permit a tool to be inserted to disassemble the device if removal becomes necessary. The connector assembly 40 can now swivel in a cone of approximately 50 degrees around the screw head. To achieve the desired position and lock it in place, rod 17 is placed between tabs 32, 33 and makes contact with collar 13. Following this action, the lock nut 16 and guide ring 15 are threaded down over tabs 32, 33 until seated firmly against rod 17. Pressure created and translated through rod 17 to collar 13 and collet 12 causes collet 12 to compress against cavity 30. As a result of screw head 20 being inserted into collet 12 during attachment, it will not allow collet 12 to compress to a diameter that will allow it to slip through cavity opening 31 because the diameter of collet 12 is greater than the diameter of the opening 31 due to the shoulder making the collet 12 a solid structure rather than a collapsible structure.

The tabs 32 and 33 are frangible at a point 57 along their length above the guide ring 15 to reduce the profile of the assembly after placement in the body. The tabs may be weakened by reduced thickness or other modification of the tabs. Further, there may be more than one level of frangibility to compensate for different surgical appliances and vertical adjustability of the placement.

Due to anatomical considerations, it is rare that a series of pedicle screws will be closely aligned once they are screwed into the vertebrae. To compensate for such misalignment, an off-set connector 14' is shown in FIGS. 2 and 3. In the preferred embodiment, the elements of sub-assembly 40' are pre-assembled. The connector 14' can be oriented through a 360 degree arc about the collet 12 and locked in place with a collar 13'. The collar 13' has an upstanding shoulder 45 with external threads 46 that engage internal threads 47 in connector 14'. The upper end of the collar 13' has a slot 48 to accept a tool (not shown) used to tighten the collar 13' and dome shaped cavity 30' of connector 14' onto the collet 12 for final assembly.

The connector 14' has an integral ring 60 with a bore 61 parallel to the opening 31' of the dome shaped cavity. The tabs 32', 33' are formed with a closed bottom 62 of a diameter to pass through the bore 61. The closed bottom 62 has a groove 63 about its circumference. After assembly, the bottom protrudes beyond ring 60 and a retaining clip 64 is resiliently seated in the groove 63 to complete the assembly. The off-set connector and screw may be preassembled before surgery to avoid handling small components in the surgical field. As mentioned above, the preferred embodiment contemplates the pedicle screw being placed in the vertebrae, alone, with subsequent assembly of the device.

In the off-set screw head 14', lock down between the screw 11 and the head 20 is accomplished by driving set screw 46 down to engage attached collar 13'. Pressure created and translated through set screw 46 onto collar 13' and collet 12' causes collet 12' to compress against cavity 30'. As a result of screw head 20' being inserted into collet 12' during attachment, it will not allow collet 12' to compress to a diameter that will allow it to slip through cavity opening 31'.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A modular polyaxial screw assembly for attaching a surgical appliance to the body comprising a screw, a swivel and a universal connector, said screw including a shaft having a helical thread thereon for securing the assembly to the bone, said shaft having a head on one end, said head tapering from a large diameter to a small diameter toward said one end of said shaft said swivel rotatably mounted on said head, said swivel being resilient, having a generally spherical outer surface and having an opening smaller than said larger diameter, said opening expanded over said large diameter and contracted thereby securing said swivel to said head, said universal connector having a generally domed shaped cavity on one end and bifurcated tabs extending therefrom, said dome shaped cavity frictionally engaging said generally spherical surface whereby said bifurcated tabs have universal movement to capture a surgical appliance therebetween.

2. A modular polyaxial screw assembly of claim 1 comprising a collar passing between said bifurcated tabs and contacting said generally spherical surface, said collar having an aperture therein, said collar providing increased surface area between said spherical surface and said dome shaped cavity.

3. A modular polyaxial screw assembly of claim 2 comprising a guide ring closely circumscribing said bifurcated tabs for support.

4. A modular polyaxial screw assembly of claim 3 comprising a locking device cooperating with said guide ring and said bifurcated tabs to connect said tabs and secure a surgical appliance in said tabs.

5. A modular polyaxial screw assembly of claim 4 comprising internal threads on said bifurcated tabs, said locking device having mating external threads to engage said tabs.

6. A modular polyaxial screw assembly of claim 4 comprising lines of weakness on said bifurcated tabs whereby said tabs are frangible adjacent said locking device to reduce the profile of the assembly.

7. A modular polyaxial screw assembly of claim 1 comprising a guide ring circumscribing said bifurcated tabs said guide ring engaging a locking device.

8. A modular polyaxial screw assembly of claim 1 comprising a locking device cooperating with said bifurcated tabs to connect said tabs and secure a surgical appliance in said tabs.

9. A modular polyaxial screw assembly of claim 8 comprising a guide ring on said locking device, said guide ring contacting said surgical appliance.

10. A modular polyaxial screw assembly of claim 1 comprising lines of weakness on said bifurcated tabs whereby said tabs are frangible adjacent said surgical appliance to reduce the profile of the assembly.

11. A modular polyaxial screw assembly of claim 1 comprising a saw flange on said head of said screw.

12. A modular polyaxial screw assembly of claim 1 comprising said universal connector including an off-set between said dome shaped cavity and said tabs.

13. A modular polyaxial screw assembly of claim 12 comprising internal threads in said dome shaped cavity, a threaded collar connecting said dome shaped cavity and said swivel, a ring about said dome shaped cavity, said ring having a bore parallel to said dome shaped cavity, said tabs protruding through said ring and locked in place.

14. A combination of a surgical appliance and a modular screw assembly, comprising a surgical appliance, a screw, a collet and a connector, said screw including a shaft having a helical thread thereon for securing the assembly to the bone, said shaft having a head on one end, said head having a driver, said head tapering from a large diameter to a small diameter toward said one end of said shaft, said collet rotatably mounted on said head, said collet having a generally spherical outer surface with at least one longitudinal slot and having an opening smaller than said larger diameter, said opening expanded over said large diameter and contracted thereby securing said collet to said head, said connector having a generally domed shaped cavity on one end and two opposing semi-circular tabs extending therefrom, said tabs internally threaded, said dome shaped cavity frictionally engaging said generally spherical outer surface, a collar removably connected to said semi-circular tabs and contacting said generally spherical outer surface, a guide ring circumscribing said semi-circular tabs, an externally threaded nut, said surgical appliance disposed in contact with said collar between said semi-circular tabs, said nut contacting said surgical appliance and threadably connected to said semi-circular tabs.

* * * * *